US00PP28772P2

(12) United States Plant Patent
Moore

(10) Patent No.: US PP28,772 P2
(45) Date of Patent: Dec. 12, 2017

(54) ***SCABIOSA* PLANT NAMED 'PMOORE02'**

(50) Latin Name: ***Scabiosa atropurpurea*×*Scabiosa caucasica***
Varietal Denomination: Pmoore02

(71) Applicant: Peter R. Moore, Stockbridge (GB)

(72) Inventor: Peter R. Moore, Stockbridge (GB)

( * ) Notice: Subject to any disclaimer, the term of this patent is extended or adjusted under 35 U.S.C. 154(b) by 35 days.

(21) Appl. No.: 14/757,199

(22) Filed: Dec. 3, 2015

(51) Int. Cl.
*A01H 5/02* (2006.01)

(52) U.S. Cl.
USPC ..... Plt./478

(58) Field of Classification Search
USPC ..... Plt./478
See application file for complete search history.

(56) References Cited

PUBLICATIONS

New Plants and Flower, Jun. 7, 2012.*

* cited by examiner

*Primary Examiner* — Keith Robinson
(74) *Attorney, Agent, or Firm* — Penny J. Aguirre

(57) ABSTRACT

A new cultivar of *Scabiosa* 'Pmoore02' that is characterized by its long flowering period, its short stature, its sterile flowers that do not produce seed, its inflorescences that are light green and turn pale pink to pale purple in color, its long lasting cut flowers, and its compact plant habit.

2 Drawing Sheets

Botanical classification: *Scabiosa atropurpurea*× *Scabiosa caucasica.*

Variety denomination: 'Pmoore02'.

BACKGROUND OF THE INVENTION

The present invention relates to a new and distinct cultivar of *Scabiosa* plant, botanically a hybrid of interspecific origin known as *Scabiosa* 'Pmoore02' and will be referred to hereafter by its cultivar name, 'Pmoore02'. The new cultivar represents a new herbaceous perennial grown for garden and landscape use.

The new invention arose from an ongoing controlled breeding program conducted by the Inventor in Longstock, England with the objective of developing new cultivars of *Scabiosa* with a non invasive plant habit that do not seed.

'Pmoore02' was derived from a cross made in 2009 between an unnamed and unpatented plant of *Scabiosa atropurpurea* plant as the female parent and an unnamed and unpatented plant of *Scabiosa caucasica* plant as the male parent. 'Pmoore02' was selected in 2010 as a single unique plant from amongst the resulting seedlings.

Asexual propagation of the new cultivar was first accomplished by the Inventor by stem cuttings in 2010 in Longstock, England. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Pmoore02' as a unique cultivar of *Scabiosa.*

1. 'Pmoore02' exhibits a long flowering period.
2. 'Pmoore02' exhibits sterile flowers and does not produce seeds.
3. 'Pmoore02' exhibits inflorescences that are light green and turn pale pink to pale purple in color.
4. 'Pmoore02' exhibits long lasting cut flowers.
5. 'Pmoore02' exhibits a compact plant habit.

The female parent differs from 'Pmoore02' in having inflorescences that are claret red in color, in having leaves that are more deeply dissected, and in producing seed. The male parent differs from 'Pmoore02' in having a less compact plant habit and in having inflorescences that are larger in size and produce seed. The Inventor is unaware of any cultivars of *Scabiosa atropurpurea*×*Scabiosa caucasica* for comparison. 'Pmoore02' can be compared to the *Scabiosa columbaria* cultivar 'Walminipink' (U.S. Plant Pat. No. 13,442) as it is similar in being long blooming and in having a compact plant habit and pink flowers. 'Walminipink' differs from 'Pmoore02' in having inflorescences that are pink throughout development and in producing reproductive organs.

BRIEF DESCRIPTION OF THE DRAWINGS

The accompanying colored photograph illustrates the overall appearance and distinct characteristics of a one year-old plant of the new *Scabiosa* as grown in a 29-cm container in Boskoop, The Netherlands.

The photograph in FIG. 1 shows a side view of 'Pmoore02' in bloom.

Figure 1:
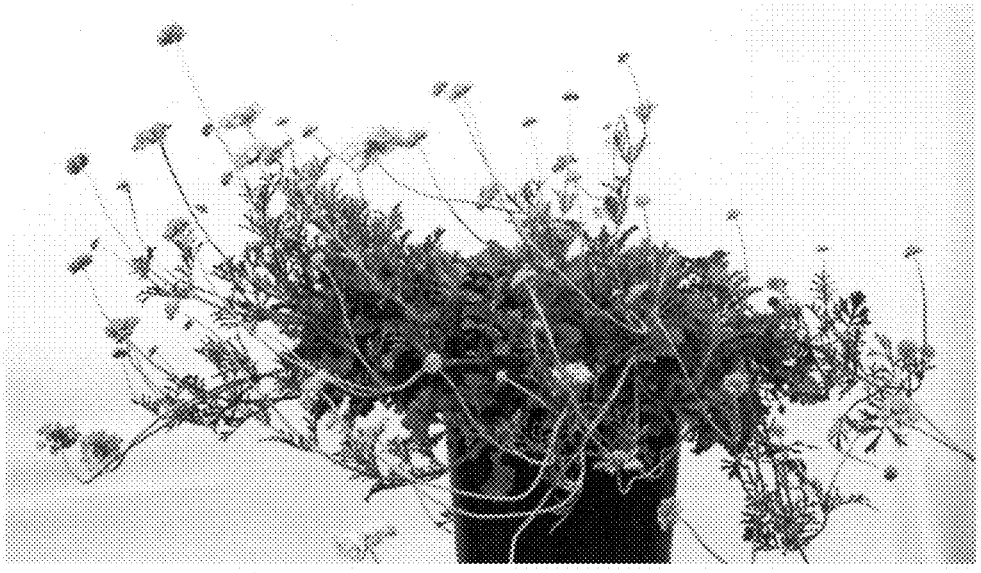
Figure 2:
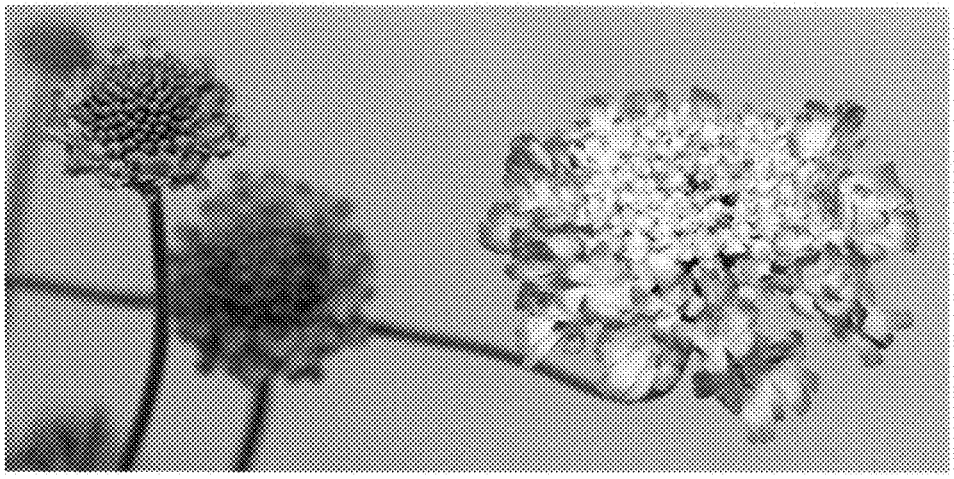

The photograph in FIG. 2 shows a close-up of the inflorescences of 'Pmoore02'.

Figure 3:
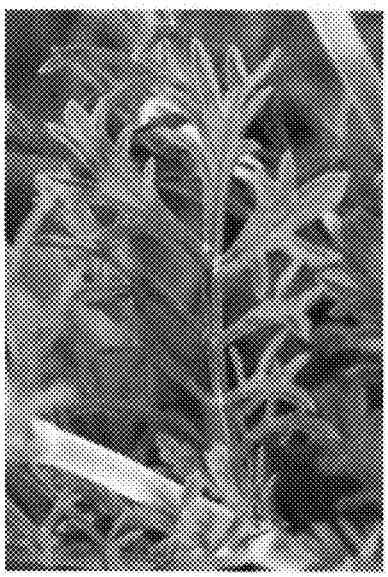

The photograph in FIG. 3 shows a close up view of a stem leaf of 'Pmoore02'.

Figure 4:
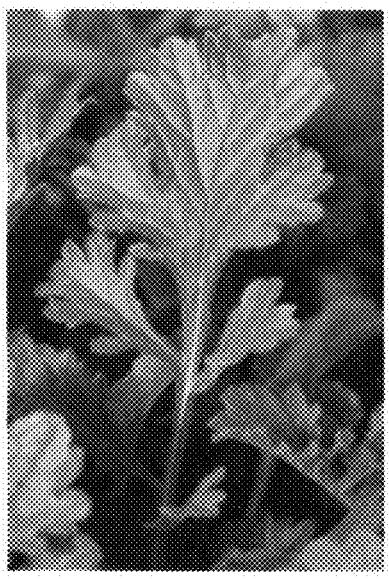

The photograph in FIG. 4 provides a close-up view of a basal leaf of 'Pmoore02'.

The colors in the photographs may differ slightly from the color values cited in the detailed botanical description, which accurately describe the colors of the new *Scabiosa*.

DETAILED BOTANICAL DESCRIPTION

The following is a detailed description of a one year-old plant of the new cultivar as grown in 29 cm containers outdoors in September in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Early summer to November in Longstock, England.

*Plant type*.—Herbaceous perennial herb.

*Plant habit*.—Compact and outward spreading, non invasive.

*Height and spread*.—Reaches an average of 30 cm in height (50 cm in bloom) and 50 cm in width for a three year-old plant in the landscape.

*Hardiness*.—Cold hardy at least to U.S.D.A Zone 5.

*Diseases and pests*.—No susceptibility or resistance to diseases or pests has been observed.

*Root description*.—Fine and fibrous, 158D in color.

*Root development*.—5 to 6 months to fully develop in a 9-cm container from a rooted cutting.

*Propagation*.—Stem cuttings.

*Growth rate*.—Moderate.

Stem description:

*Stem shape*.—Rounded.

*Stem color*.—143B, upper side tinged 147A.

*Stem size*.—Main stems; average of 35 cm in length (excluding inflorescence) and 2.75 mm in diameter, lateral branches; average of 8.2 cm in length (excluding inflorescence) and 2.75 mm in diameter.

*Stem amount*.—Average of 56 main stems with an average of 7 lateral (flowering) stems each.

*Stem surface*.—Slightly glossy and densely covered with short soft hairs average of 0.3 mm in length and NN155D in color.

*Stem aspect*.—Lateral stems held at an average angle of 30° to the main stem.

*Stem strength*.—Strong.

*Branching habit*.—Moderate, main stems grow from the base with some lateral stems.

*Internode length*.—Average of 6.2 cm.

Foliage description:

*Leaf division*.—Simple.

*Leaf shape*.—Obovate.

*Leaf base*.—Truncate.

*Leaf apex*.—Basal leaves and lower stem leaves short acute to retuse, upper stem leaves acute.

*Leaf margin*.—Basal leaves and lower stem leaves pinnatifid to pinnatisect, lobes broad and with rounded tips, upper stem leaves pinnatisect, lobes narrow and with acute tips.

*Leaf venation*.—Pinnate, upper surface of basal and stem leaves 144A in color, lower surface of basal and stem leaves 146B to 146C in color.

*Leaf attachment*.—Petiolate.

*Leaf arrangement*.—Opposite.

*Leaf surface*.—Both sides slightly glossy, soft to the touch due to leaf pubescence, leaves densely covered with short soft hairs average of 0.5 mm in length and NN155D in color.

*Leaf color*.—Pinnate, young upper surface; basal leaves and lower stem leaves 144B, upper stem leaves 143A, young lower surface; basal leaves and lower stem leaves 145A, upper stem leaves 143B, mature upper surface; basal leaves and lower stem leaves 137B to 137C, upper stem leaves 137B, mature lower surface; basal leaves and lower stem leaves in between 143C and 144A, upper stem leaves in between 143A and 144A.

*Leaf size*.—Basal leaves and lower stem leaves an average of 8.8 cm in length and 3.7 cm in width, upper stem leaves 7.2 cm in length and 4.4 cm in width.

*Leaf number*.—Average of 12 per lateral stem.

*Leaf fragrance*.—None.

*Petiole*.—Basal leaves and lower stem leaves; an average of 3.7 cm in length, 2 mm in diameter, 143B in color, upper stem leaves; an average of 3 mm in length and 3 mm in diameter, 143B and tinged with 182B to 182C in color, surface lightly pubescent.

Flower description:

*Inflorescence type*.—Terminal capitulum.

*Lastingness of inflorescence*.—Average of 7 days.

*Lastingness as a cut flower*.—About 7 days in a vase in water.

*Inflorescence size*.—An average of 3.1 cm in height and 5.8 cm in diameter.

*Inflorescence fragrance*.—None.

*Flower number*.—Average of 115 flowers per inflorescences.

*Flower form*.—Singular marginal flowers larger and more conspicuous than central flowers, funnel-form, in marginal flowers the lower 65% of the petals are fused into a tube, in central flowers the lower 85% of the petals are fused into a tube.

*Flower aspect*.—Upright to outward.

*Flower buds*.—Average of 4 mm in length, average of 1 mm in diameter, 145B in color, top tinged 182D, obovate in shape.

*Flower size*.—Marginal flowers; 1.6 cm in diameter, 2.7 cm in height, central flowers; 5.5 mm in length, 1 cm in height.

*Petals*.—5, texture is dull and smooth on both sides, rotate in arrangement, marginal flowers; 65% of the petal is fused into a tube, petals spathulate in shape, lower three petals considerably larger than the upper two petals, margins entire, apex is praemorse to crispate in shape, lower 3 petals an average of 2.7 cm in length and 4 mm in width, upper 2 petals an average of 1.8 cm in length and 3 mm in width, color: when opening upper surface; 145C, tip tinged 182B, tube N155B, when opening lower surface; 145C, tube N155B, when fully open upper surface; 75C, tip tinged 176B to 182B, tube N155B, when fully open lower surface; 75D, tip tinged 145C and 184B, tube N155B, central flowers; 85% of the petal is fused into a tube, petals oblanceolate in shape, margins entire, apex is rounded, moderately covered with very short hairs an average of 0.3 mm in length and NN155D in color, average of 1 cm in length and 2 mm in width, when opening upper surface; 69D, tube N155B, when opening lower surface; 145C, 69D, tinged 145C, tube N155B, when fully open upper surface; 75C, tip 184B, tube is N155B, when fully open lower surface; 75D, tinged 145C, tube is N155B.

*Petaloid.*—5, surfaces dull and smooth, rotate in arrangement, oblanceolate in shape, entire margins, marginal flowers; 2.4 cm in length and 4 mm in width, color: immature surfaces; 145C, tip tinged 182B, mature surfaces; 63C to 70B to 70C, tip tinged 146B to 146C, central flowers; 1 cm in length, 0.5 mm in width, color: immature surfaces; 69D, mature surfaces; 75C, tips 184B.

*Calyx.*—Rotate in shape, an average of 9 mm in length and 7 mm in diameter.

*Sepals.*—5, linear in shape, an average of 9 mm length, 0.5 mm in width, entire margin, smooth and slightly glossy surface, narrow acuminate apex, fused base lower 8%, immature and mature upper and lower surface color; 182B, base 145B.

*Peduncles.*—An average of 23.9 cm in length and 3 mm in diameter in width, held straight on top of stem, strong in strength, 138B in color, surface slightly glossy and densely covered with short soft hairs average of 0.3 mm in length and NN155D in color.

*Pedicels.*—None.

*Involucral bracts.*—An average of 16, linear in shape, apex acute, about 9 mm in depth and 2 mm in width, color; both sides 137A, base 144B, surface is moderately covered with thin hairs; an average of 0.5 mm in length and NN155D in color.

Reproductive organs:

*Gynoecium.*—No pistils present.

*Androcoecium.*—No stamens present.

*Fruit/seeds.*—No seeds have been observed to date, observed to be sterile.

It is claimed:

1. A new and distinct cultivar of *Scabiosa* plant named 'Pmoore02' as herein illustrated and described.

* * * * *